United States Patent [19]
Ryley et al.

[11] Patent Number: 5,724,151
[45] Date of Patent: Mar. 3, 1998

[54] WAVEGUIDE SENSING ELEMENT FOR USE IN A SAMPLE MEDIUM AND METHOD OF REAR-FIRING ELECTROMAGNETIC RADIATION

[75] Inventors: James Francis Ryley, Drexel Hill; Joseph Anthony Perrotto, Landenberg, both of Pa.; Moshe Oren, Waltham, Mass.; Ronald Jack Riegert, Newark, Del.

[73] Assignee: E.I. du Pont de Nemours and Company, Wilimington, Del.

[21] Appl. No.: 688,450

[22] Filed: Jul. 30, 1996

Related U.S. Application Data

[60] Provisional application No. 60/001,807, Aug. 4, 1995.
[51] Int. Cl.⁶ .................................................. G01N 21/00
[52] U.S. Cl. ........................... 356/432; 356/320; 356/317
[58] Field of Search ........................... 356/432, 320, 356/317, 39

[56] References Cited

U.S. PATENT DOCUMENTS

| | | | |
|---|---|---|---|
| 3,967,877 | 7/1976 | Heidrich et al. | 350/96 C |
| 4,829,186 | 5/1989 | McLachlan et al. | 250/373 |
| 4,877,747 | 10/1989 | Stewart | 356/432 |
| 4,880,752 | 11/1989 | Keck et al. | 356/417 |
| 5,082,629 | 1/1992 | Burgess, Jr. et al. | 422/82.11 |
| 5,243,676 | 9/1993 | Bierlein et al. | 385/122 |
| 5,359,681 | 10/1994 | Jorgenson et al. | 356/320 |

FOREIGN PATENT DOCUMENTS

| | | | |
|---|---|---|---|
| 0 221 011 | 9/1986 | European Pat. Off. | G01N 21/55 |
| 43 33 560 | 4/1995 | Germany | G01N 21/31 |
| 2 186 387 | 8/1987 | United Kingdom | G02B 6/00 |
| 2 228 083 | 8/1990 | United Kingdom | G01N 21/01 |
| 2 276 003 | 9/1994 | United Kingdom | G01N 21/03 |
| WO 91/10122 | 7/1991 | WIPO | G01N 21/00 |
| WO 92/03720 | 3/1992 | WIPO | G01N 21/75 |
| WO 94/28395 | 12/1994 | WIPO | G01N 21/43 |

OTHER PUBLICATIONS

D.G. Dalgoutte et al., "Thin grating couplers for integrated optics: an experimental and theoretical study", *Applied Optics*, 14, (12), 2983–2998, Dec. 1975.

Christophe Piraud et al., "Optoelectrochemical Transduction on Planar Optical Waveguides", *Journal of Lightwave Technology*, 10, (5), 693–699, May, 1992.

R.C. Hughes, et al., "Chemical Microsensors", *Science*, 254, 74–80, Oct. 4, 1991.

Don S. Goldman, "Planar Waveguide Spectrometer For Process Analysis", *Sensors*, 21–25, Oct. 1991.

(List continued on next page.)

*Primary Examiner*—Frank G. Font
*Assistant Examiner*—Reginald A. Ratliff
*Attorney, Agent, or Firm*—Jane Obee Hamby

[57] ABSTRACT

A waveguide sensing element has a substrate having an input opening adapted to house an input optical fiber and an output opening adapted to house an output optical fiber. The input optical fiber transmits electromagnetic radiation, and the output optical fiber emits the electromagnetic radiation. The waveguide sensing element also has a guiding layer disposed adjacent the substrate. The guiding layer has a beveled end face. The angle of the bevel is chosen so that the guiding layer selects only those modes within a given range—i.e., high order modes. This increases the spectral absorption measurement sensitivity as compared to a waveguide sensing element which uses the complete mode spectrum. Such a highly sensitive waveguide sensing element has been found to be particularly useful as an internal reflection spectroscopic sensing element. Moreover, the waveguide sensing element of the present invention is particularly useful in a process environment, where the corrosive effects of chemicals make on-line spectral absorption measurements difficult. Thus, the waveguide sensing element of the present invention may be rear-fired, which is particularly attractive from a process seal integrity standpoint.

27 Claims, 5 Drawing Sheets

OTHER PUBLICATIONS

Michael D. DeGrandpre et al., "Thin Film Planar Waveguide Sensor For Liquid Phase Absorbance Measurements", *Analytical Chemistry*, 62, (18), 2012–2017, Sep. 15, 1990.

P.K. Tien et al., "Experiments on Light Waves In A Thin Tapered Film and A New Light–Wave Coupler", *Applied Physics Letters*, 18, (9), 396–401, May 1, 1971.

Dennis A. Stephens et al., "Absorption Spectrometry of Bound Monolayers on Integrated Optical Structures", *Anal. Chem.*, 61, 386–390, 1989.

W.M.K.P. Wijekoon et al., "Ethylene adsorption on ZnO: CARS spectroscopy with optical waveguides", *J. Chem. Phys.*, 86, (8), 4384–4390, Apr. 15, 1987.

Y. Kokubun et al., "Silicon Optical Printed Circuit Board for Three–Dimensional Integrated Optics", *Electronics Letters*, 21, (11), 508–509, May 23, 1985.

Thomas Register 1991, Sight Glasses, "PresSure™".

Baumeister et al., Marks'Standard Handbook for Mechanical Engineers, "Gaskets and Seals", 26.26–26.27, Packing and Seals, 8–145, Eighth Edition, McGraw Hill.

WAVEGUIDE SENSING ELEMENT FOR USE IN A SAMPLE MEDIUM AND METHOD OF REAR-FIRING ELECTROMAGNETIC RADIATION

This application claims the priority benefit of U.S. Provisional application Ser. No. 60/001,807, filed Aug. 4, 1995.

BACKGROUND OF THE INVENTION

1. Field of the Invention

The present invention relates to a waveguide sensing element for use in a sample medium. More specifically, the present invention relates to a waveguide sensing element having a beveled end face, where the angle of the bevel is chosen so that the guiding layer selects only those modes within a given range, i.e., high order modes. This allows the sensing element to be rear-fired, which feature is useful in a chemical manufacturing environment.

2. Description of the Related Art

Process control of chemical systems has become increasingly more sophisticated over the years. Spectral absorption measurements have long been used to determine concentrations and identify components of such chemical systems. These measurements were typically made off-line in laboratories. The ability to perform these measurements on-line is becoming increasingly important, since it allows for closed loop control of processes. The reduction in sample analysis turn-around time resulting from on-line measurement translates to higher yield, higher product quality, and reduced by-product. On-line spectroscopic equipment for many applications is readily available. However, current commercial devices do not effectively address some important process areas, such as those requiring low and medium absorbance measurements in the presence of particulates. Moreover, a problem associated with on-line analysis in chemical systems is that the chemicals of such systems, because of their contact with the sensing element, corrode the components of the sensing element.

Spectroscopic absorption measurements are typically made by direct transmission techniques, i.e., the entire probe signal is transmitted directly through the sample medium to be measured. However, high concentrations of particulates generate excessive scattering, which makes transmission techniques difficult. In addition, high absorbances of the sample require very short path lengths in transmission techniques to preserve signal strength. Such short path lengths are generally not feasible when using manufacturing-scale equipment.

Spectroscopic measurements may also be made via absorption of a guided signal by way of an evanescent wave produced adjacent to (outside) a dielectric wave guide. Solution of the wave equation with appropriate boundary conditions demonstrates that, assuming the guiding layer has a higher index of refraction than the surrounding media, the majority of propagated radiation will be confined by the guiding layer surface(s). However, a small amount penetrates this surface into the surrounding media.

The intensity of this radiation outside the guide surface decays exponentially with distance from the guide surface and is termed the "evanescent wave". The attenuation of the evanescent wave is in principle equivalent to the attenuation experienced in direct transmission. However, the evanescent wave carries only a small fraction of the guided signal's total power. As the evanescent wave is absorbed by the sample medium surrounding the guide, it is continually replenished by the power within the guiding layer. Thus, the absorption of the power contained in the evanescent wave results in a reduction in guided energy. It is the small fractional power contained within the evanescent wave, and its exponential decay with distance from the surface of the guiding layer, that enable internal reflection spectroscopy (IRS) to address certain applications that fall outside the capabilities of direct transmission spectroscopy, such as measurement of media having a high concentration of particulates, or media having high absorbances.

However, conventional IRS has its limitations. Because it interfaces directly with the process stream through an evanescent field, the sensitivity per unit length is reduced, compared to transmission techniques. Reduced sensitivity is desirable for highly absorbing applications, but becomes a problem in medium or low-absorbance cases. In such cases, analytes that are not strongly absorbing may not be detectable at the desired concentration levels.

In known guiding layers, radiation is coupled into the guiding layer so that it is propagated down the axis of the guiding layer. Optical propagation through a planar guiding layer occurs in discrete modes, which are characterized by the angle between the mode's propagation vector and the guiding layer axis. The guiding layer dimension in the vertical direction can be selected to allow only one mode or many modes to propagate in the waveguide. The guiding layer dimension can range anywhere from a few thousand angstroms (single-mode operation) to hundreds of microns (multi-mode operation).

A single-mode guiding layer, operating near cutoff, in theory, would be effective for spectroscopic measurement. All power could be concentrated in the single propagating mode and that mode could have a relatively long evanescent wave. However, coupling radiation from an extended source into such a small target is extremely difficult. Furthermore, the unavailability of single-mode, mid-IR optical fibers make the remote location of source and detector impractical for spectroscopic measurement in the region beyond 2 µm. A typical approach to this coupling problem is to end fire, or butt couple, a beam of radiation into a guiding layer. However, a butt-coupled design considerably complicates the problem of sealing the sensing element/sample medium interface.

Off-axis launching methods have also been devised. These include the use of prisms to match the propagation constant for allowed guiding layer propagation modes. However, using prisms has disadvantages. The need to maintain a precise, tapered space between the prism and the guiding layer makes design of a robust assembly difficult. Also, the choice of prism materials is limited, since the prism must have a higher index of refraction than the guiding layer, which must be higher than the refractive index of the sample medium. Light can also be launched at a non-normal angle as disclosed in U.S. Pat. No. 3,967,877.

Yet another approach to launching light is "rear firing", where electromagnetic radiation is directed normal to the guiding layer axis through the substrate and any optical buffer layer that may be present. This type of configuration is attractive from a process seal integrity standpoint. U.S. Pat. No. 5,082,629 to Burgess et al. describes the use of entrance and exit "gratings" to couple rear-fired light into and out of a guiding layer. Proper grating design can efficiently couple selected wavelengths into the guiding layer. However, gratings as described by Burgess et al. experience loss of signal intensity and are relatively inefficient for broad-band sources. In addition, accurate, high-efficiency gratings are also difficult and costly to fabricate.

Thus, there exists a need for efficient, inexpensive coupling of light into a guiding layer in a manner that facilitates the use of the guiding layer in an internal reflection spectroscopic sensing element. Such a sensing element would be particularly useful in chemical manufacturing environments, where the corrosive effects of the chemicals make on-line spectral absorption measurements difficult. It would be particularly desirable from a process seal standpoint to be able to rear-fire electromagnetic radiation into such a guiding layer, without sacrificing the sensitivity of the sensing element.

SUMMARY OF THE INVENTION

The present invention solves the problems of the prior art by recognizing that, in low absorbance cases, it is desirable that the majority of high order modes are captured within the guiding layer, and that it is beneficial in such cases to selectively couple only such high order modes. Accordingly, the present invention provides a guiding layer which selectively couples only high order modes. Since only high order modes are selectively coupled, the present invention achieves increased spectral absorption measurement sensitivity as compared to a waveguide sensing element that uses the complete mode spectrum.

Moreover, the highly sensitive waveguide sensing element of the present invention has been found to be particularly useful as an internal reflection spectroscopic sensing element. The waveguide sensing element of the present invention therefore has particular utility in a process environment, where the corrosive effects of chemicals make on-line spectral absorption measurements difficult. Thus, the present invention overcomes the problems associated with butt coupling, which can be difficult in a process environment.

Moreover, such a highly sensitive waveguide sensing element allows electromagnetic radiation to be rear-fired into the waveguide sensing element, which is attractive from a process seal integrity standpoint. In this way, the present invention overcomes the problems of loss of signal intensity and inefficiency when used with broad-band sources experienced by gratings.

Also, the present invention provides a design for a waveguide sensing element which is easily fabricated. In addition, the waveguide sensing element of the present invention is wavelength insensitive.

Furthermore, the design of the present invention encases optical fibers and protects them from a process fluid, which is especially important when used in a corrosive environment.

Thus, in accordance with the purposes of the invention as embodied and broadly described herein, there is provided a waveguide sensing element for detecting a component in a sample medium, comprising: a substrate having an input opening adapted to accept an input optical fiber and an output opening adapted to accept an output optical fiber, wherein the input optical fiber transmits rear-fired electromagnetic radiation and the output optical fiber emits the rear-fired electromagnetic radiation; and a guiding layer disposed adjacent to the substrate, the guiding layer having a longitudinal axis, a first surface, a second surface spaced from the first surface, and bevel means extending between the first surface and the second surface for directing the rear-fired electromagnetic radiation along the longitudinal axis of the guiding layer.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description serve to explain the principles of the invention.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

In accordance with a first embodiment of the present invention, there is provided a waveguide sensing element for analyzing a component in a sample medium. It should be noted that the waveguide sensing element of the present invention can be used to analyze more than one component at a time. Moreover, the medium may be a liquid, gas or solid. If it is a solid, the solid must be conformable to the guiding layer. In a preferred embodiment, the waveguide sensing element of the present invention is used to analyze analytes in a process fluid used in a chemical manufacturing environment, where corrosive chemicals in the fluid destroy the components of the sensing element and make on-line spectral absorption measurements difficult. In such environments, the substrate is particularly sensitive, and the guiding layer must be resistive to chemicals. However, it should be understood that the utility of the waveguide sensing element of the present invention is not limited to such environments, and can be used in a broad spectrum of applications.

Figure 1:
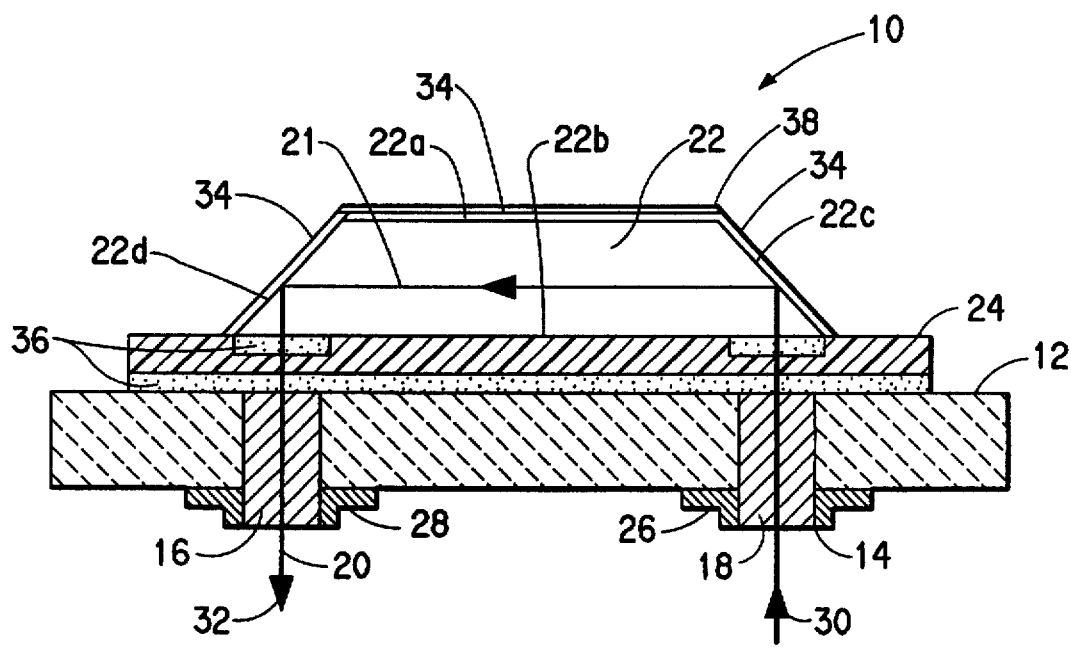
FIG. 1 is a cross-sectional view of a waveguide sensing element according to a first embodiment of the present invention.

A waveguide sensing element according to the first embodiment of the present invention is shown generally at 10 in FIG. 1. Waveguide sensing element 10 comprises a substrate 12 having an input opening 14 and an output opening 16. Input opening 14 is adapted to accept an input optical fiber 18, and output opening 16 is adapted to accept an output optical fiber 20. Fiber 18 transmits electromagnetic radiation, and in particular, rear-fired electromagnetic radiation, via input opening 14, and fiber 20 emits the rear-fired electromagnetic radiation via output opening 16. The electromagnetic radiation emitted from fiber 20 is sent to a detector, not shown. Each fiber may be surrounded by a ferrule, also not shown.

Figure 2:
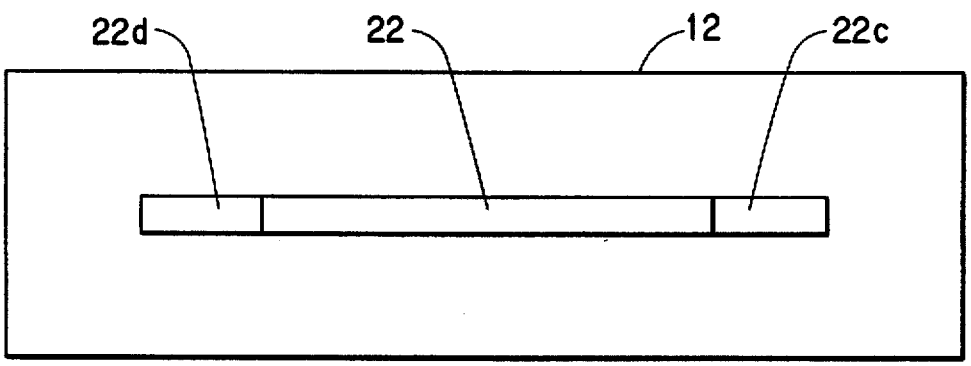
FIG. 2 is a top view of the guiding layer and substrate of the waveguide sensing element as shown in FIG. 1, except that the coatings and the buffer layer are not shown.

The waveguide sensing element of the present invention also comprises a guiding layer 22 as shown in FIGS. 1 and 2 disposed adjacent to the substrate. The shape of the guiding layer of the present invention may be generally rectangular, e.g., what is commonly called a ridge waveguide. Other shapes such as planar and buried waveguides could also be used for the guiding layer. It is conceivable that even various microwave designs, such as stripline and microstrip designs, may also be used with the present invention.

The guiding layer does not usually have sufficient structural strength to be free-standing and therefore must be supported on a substrate of some kind. If the substrate material has suitable optical properties (i.e., it is transmissive and its index of refraction is less than that of the guiding layer), it can serve as the lower cladding material for confining optical energy in the guiding layer. Otherwise, a buffer layer is necessary between the guiding layer and the substrate. Thus, the waveguide sensing element of the present invention may further comprise a buffer layer disposed between the guiding layer and the substrate. A buffer layer 24 as shown in FIG. 1 may be deposited between guiding layer 22 and substrate 12. Buffer layer 24 must be fairly transmissive in the wavelength regions of spectroscopic interest, which depend on the component being analyzed, to avoid unnecessary signal attenuation at these wavelengths. The substrate of the present invention is often a ceramic material, but can comprise other materials such as glasses, metals or semiconductors. Generally, it is also preferred that the substrate be resistant to chemicals in the sample medium in which the waveguide sensing element of the present invention is used, if it is used in a corrosive environment.

Fibers 18 and 20 are connected at any given angle to guiding layer 22 by a respective fiber connector 26 and 28. Preferably, the fibers are connected orthogonally, as this is the easiest configuration to machine. Connectors, such as standard SMA (stripline microwave type A threaded) connectors, can be used for fiber connectors 26 and 28. A metal fitting may be used between the substrate and connectors 26, 28 to provide a mechanically robust connection point. The connectors may be made of a low-expansion alloy, sold under the trademarks KOVAR® or INVAR®, (hereinafter referred to as KOVAR® or INVAR®) to match the characteristics of the substrate. Alloys such as KOVAR® or INVAR® normally have low corrosion resistance but can be used in the waveguide sensing element of the present invention since they will not contact the sample medium. The fitting may be separate from the substrate, or may be bonded on the substrate. Alternatively, the connectors themselves may be machined into the substrate. The connectors are generally attached to the substrate by brazing or other suitable methods.

The guiding layer of the present invention has a longitudinal axis 21 as shown in FIG. 1. The guiding layer also has a first surface 22a and a second surface 22b spaced from first surface 22a as shown in FIG. 1. The guiding layer also has bevel means extending between the first surface and the second surface for directing the rear-fired electromagnetic radiation along the longitudinal axis of the guiding. The bevel means comprises a beveled end face, a plurality of which are shown at 22c and 22d in FIGS. 1 and 2. The beveled end face of the present invention may have various configurations. For example, it may be either flat or cupped. The angle of the bevel is shown in FIG. 1 as the same at both beveled end faces, although it does not have to be. It will be apparent to those skilled in the art that various modifications and variations can be made in the construction of the waveguide sensing element of the present invention without departing from the scope or spirit of the invention. As an example, the waveguide sensing element of the present invention could be designed to employ only one optical fiber, provided the optical fiber has a beam splitter to separate the incident beam from the exiting beam. In this situation, the guiding layer would then comprise a single beveled end face such that the optical fiber is positioned opposite the single beveled end face.

Figure 3:
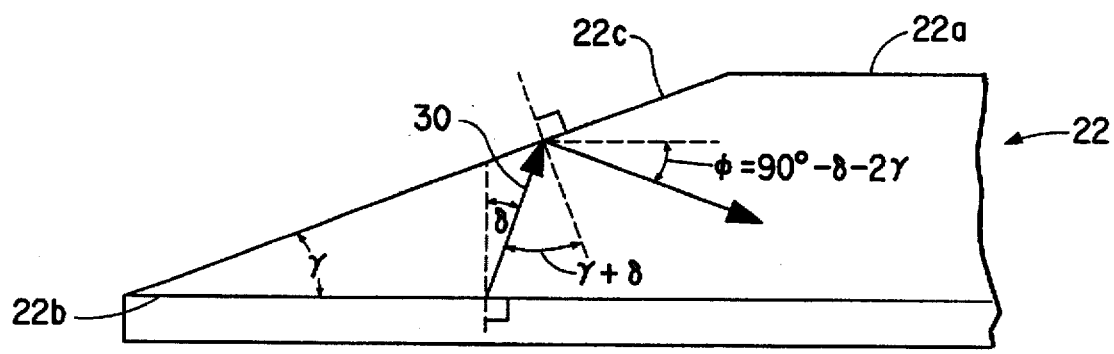
FIG. 3 is a partial, cut-away view of a guiding layer and an optical fiber, similar to those shown in FIG. 1 and illustrating the geometry of the guiding layer and the paths of the beams of electromagnetic radiation.

FIG. 3 is a partial, cut-away view of a waveguide sensing element, similar to that shown in FIG. 1, but with the incoming beam of radiation at the left of the figure instead of the right. Beveled end face 22c is shown, extending between first surface 22a and second surface 22b. In FIG. 3, $\delta$ is the angle at which an incoming beam exits the fiber and enters the waveguide. A bevel angle, $\gamma$, also referred to as the beveled end face angle, is the angle between beveled end face 22c and second surface 22b. A propagation angle, $\phi$, as shown in FIG. 3, is the angle between the axis of the guiding layer and the direction of propagation of the wave of electromagnetic radiation. As can be seen from FIG. 3, $\phi=90°-\delta-2\gamma$.

Figure 4:
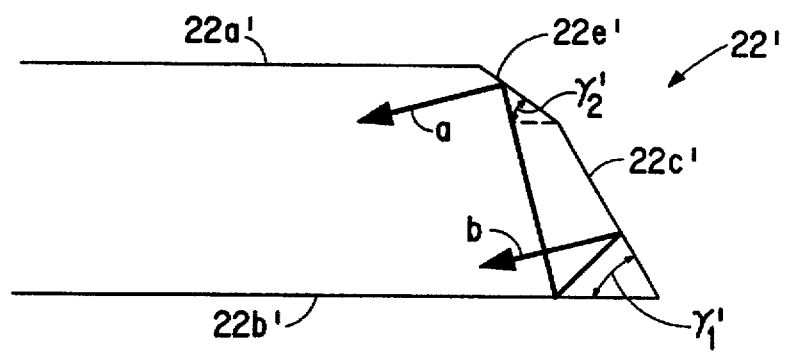
FIG. 4 is a partial, schematic view of an alternative configuration of a guiding layer, showing a multi-faceted beveled end face.

FIG. 4 shows an alternative configuration of a guiding layer 22' according to the present invention, which has a first surface 22a', a second surface 22b' and a beveled end face which is compound in nature, i.e., multi-faceted. As shown in FIG. 4, end faces 22c' and 22e' together extend between a first surface 22a' and a second surface 22b'. This allows different portions of the input beam to be affected differently. End face 22c' forms a bevel angle $\gamma_1'$ with surface 22b', and end face 22 e' forms a bevel angle $\gamma_2'$ with a plane parallel to surface 22b'. Such a multi-faceted bevel might, for instance, convert two widely diverging incoming beams, such as incoming beams a and b shown in FIG. 4, into two nearly co-directional rays. Thus, it would be possible to convert some low order modes to high order modes while retaining modes that were originally of high order. The converse case, converting high order to low order, would also be possible.

Figure 5:
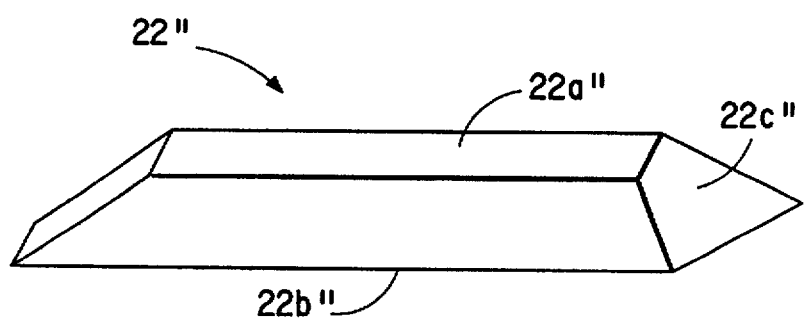
FIG. 5 is a perspective view of a further alternative configuration of a guiding layer, showing the end face tilted in both the azimuthal and polar angles.
Figure 6:
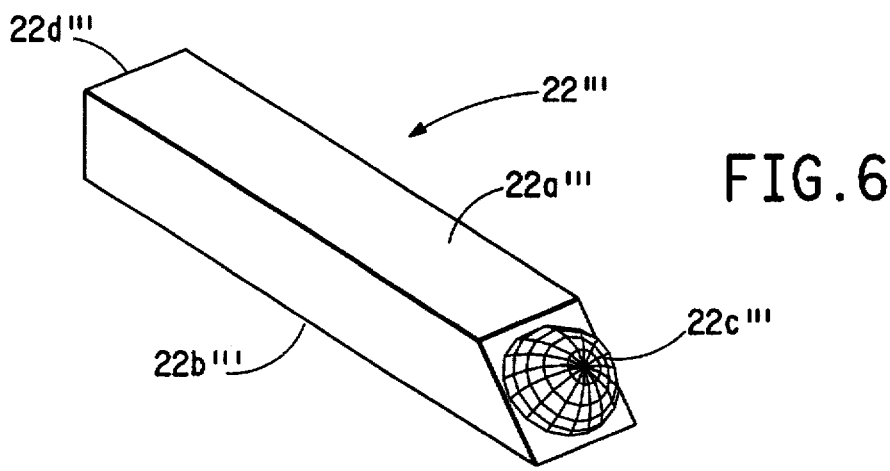
FIG. 6 is a perspective view of another further alternative configuration of a guiding layer, showing the end face shaped to provide a lensing/focusing effect.

The beveled end face might also be tilted in both the azimuthal and polar angles, as shown at 22c" for the right hand face of a guiding layer 22" as shown in FIG. 5. Guiding layer 22'" has a first surface 22a" and a second surface 22b". This tilted beveled end face of FIG. 5 would cause a ray entrant from below and reflecting off this face to take a helical path down the wave guide. Such a path might be advantageous for when the waveguide is used as a sensing element, since it would allow more efficient use of the sidewall portions of the waveguide. A further alternative configuration for the guiding layer of the present invention is shown at 22''' in FIG. 6 and includes a first surface 22a''' and a second surface 22b'''. In such a guiding layer, the end face(s) might also be shaped to provide a lensing/focusing effect as shown in FIG. 6, such as end face 22c'''. Such a lensed face could, in principle, convert most of the modes injected from an optical fiber into a single waveguide mode.

The waveguide sensing element of the present invention is a multi-mode device that is, in particular, suitable for spectroscopic measurement in the region beyond 2 μm. It works based on the principles of internal reflection spectroscopy (IRS) by spectroscopically sampling a medium through the evanescent wave which is produced when electromagnetic radiation is propagated along the longitudinal axis of the guiding layer. Beveled end face 22c reflects the incoming, or incident beam of electromagnetic radiation, which is shown in FIG. 1 at 30, and changes the angle of the incident beam by reflection. The beveled end face re-directs the electromagnetic radiation so that the radiation propagates along the longitudinal axis of the guiding layer. The exiting beam, which is shown at 32 in FIG. 1, is reflected out of the guiding layer by beveled end face 22d.

Figure 7:
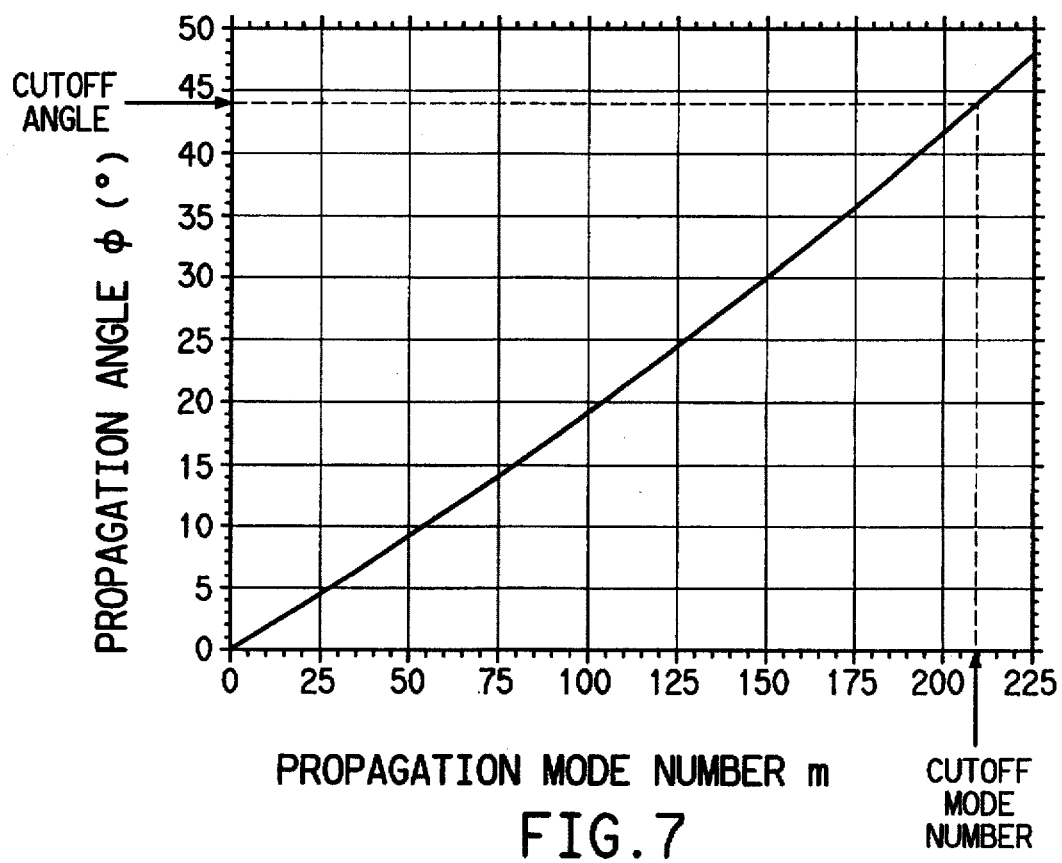
FIG. 7 is a graph showing propagation angle vs. propagation mode number of a planar waveguide sensing element immersed in 50 ppm DCB in DCA.

It is well known that only a finite number of discrete modes are propagated by the guiding layer. These modes can be associated with specific propagation angles as illustrated with reference to FIG. 7. FIG. 7 shows a propagation mode number, m, vs. propagation angle $\phi$, in degrees at $\lambda=7.41$ μm for a planar waveguide with a guiding layer comprising 500 μm zinc sulfide, a buffer layer comprising 5 μm yttria and a substrate comprising alumina, immersed in 50 ppm DCB in a reagent of DCA having a refractive index of 1.6. Applicants modeled the waveguide sensing element of the present invention as having four layers: the substrate layer, of refractive index $n_S$, the buffer layer of refractive index $n_B$, the guiding layer of refractive index $n_G$ and the surrounding sample medium of refractive index $n_C$. It was assumed that the refractive index of the chemical system is less than that of any of the other layers. Applicants have shown that some of these modes are much more sensitive than others to the surrounding chemical system, or sample medium.

Figure 8:
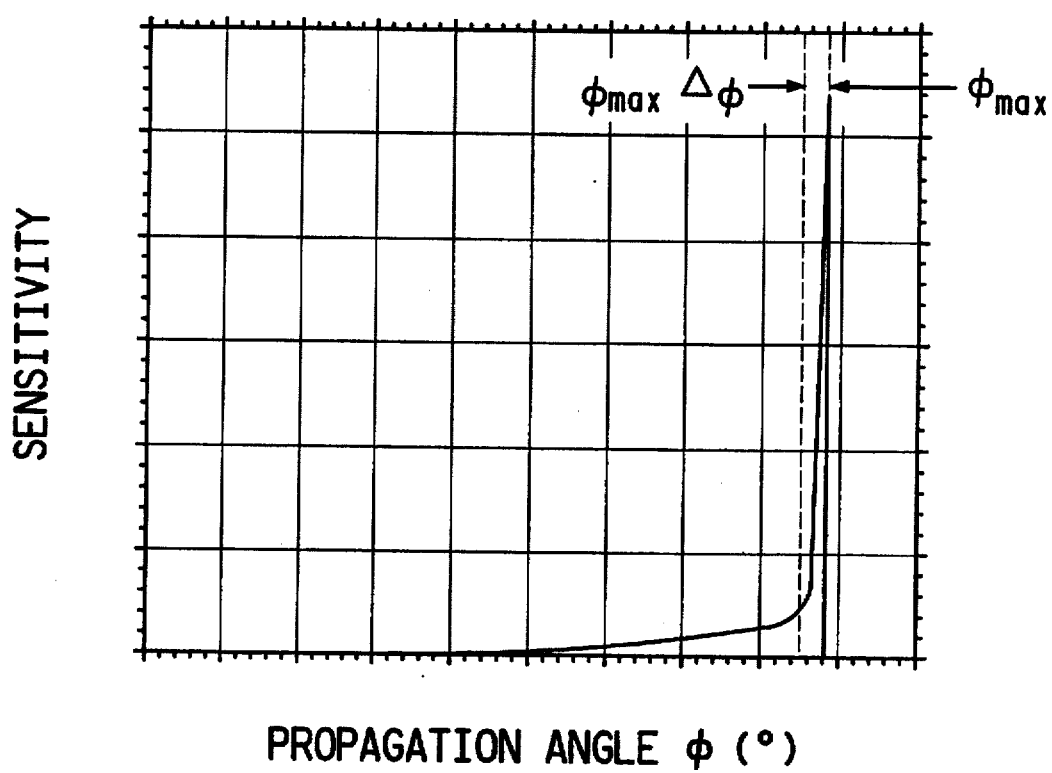
FIG. 8 is a graph showing predicted sensitivity of absorption loss to changing chemical concentration as a function of propagation angle for the waveguide sensing element as described with respect to FIG. 7.

From this model the characteristics, such as evanescent wave penetration depth and percent of total mode power contained in an evanescent wave, can be computed. With this information, an effective modal absorption coefficient can be calculated. From this, a plot of the change in absorption coefficient with change in concentration, $d\alpha(\phi)/dC$, may be made. This sensitivity to change in concentration is the quantity of interest in spectroscopic applications. FIG. 8 shows such a plot for a zinc sulfide guiding layer immersed in 50 ppm DCB in DCA. The sudden decided upswing in the curve indicates that there is, in fact, a relatively small group of modes that are considerably more sensitive than others. It is therefore advantageous, from a system sensitivity standpoint, to use only the modes within some small $\Delta\phi$, or given range, that make up the steep portion of the curve. These modes are high order modes. High order modes are those with more acute angles formed between the mode's propagation vector and the guiding layer axis. The high order modes also have a larger portion of their total power residing in the evanescent wave. Thus, in accordance with the present invention, the angle of the bevel is chosen so that only those modes within a given range, that is, high order modes, are selected by the guiding layer. This results in increased spectral absorption measurement sensitivity as compared to a waveguide sensing element that uses the complete mode spectrum. Such a highly sensitive waveguide sensing element has been found to be useful as an internal reflection spectroscopic sensing element. The waveguide sensing element of the present invention is particularly useful in a process environment, where the corrosive effects of chemicals make on-line spectral absorption measurements difficult. Thus, the waveguide sensing element of the present invention may be rear-fired, which results in the beveled end face directing rear-fired electromagnetic radiation along the longitudinal axis of the guiding layer.

In the waveguide sensing element of the present invention, special consideration must be given to the coupling of the extended light source (not shown), which emits electromagnetic radiation, to the guiding layer. Whether reflective or refractive, a focusing system of some kind is necessary. Optical fibers, available commercially with core sizes on the same scale of the film guiding layer, e.g., approximately 500 μm, allow the remote location of both the extended light source and detector, but also allow the components of the focusing system to be remoted with the source.

The choice of materials for the guiding layer is an important consideration in designing the waveguide sensing element of the present invention. Certain parameters, such as resistance to chemical attack and optical transmission properties in the frequency region of interest, are prime considerations. Other properties such as hardness, refractive index, and coefficient of thermal expansion also play an important role and must be considered. The refractive index of the guiding layer must be higher than the refractive index of all the adjacent materials, i.e., the surrounding medium being analyzed and the buffer layer, or the substrate if no buffer layer is present. It should be noted that, with the present invention, if the difference in refractive indices between the guiding layer and the surrounding medium is sufficient, mirroring of the end faces is not necessary.

In light of the constraint that the refractive index of the guiding layer must be higher than the refractive index of all the adjacent materials, the use of a thin-film guiding layer greatly expands the spectrum of available materials. A drawback to using IRS with bulk sensing elements is that the materials of construction for the sensing element are limited to transmissive materials available in bulk form of sufficient size, typically about ¼ to ½ inches (0.635 to 1.27 cm.) in diameter and about 4 to 6 inches (10 to 15 cm.) in length. Currently, only about ten materials are known which will work in the mid-IR range. There are many more transmissive materials available as thin films. This expanded spectrum of available guiding layer materials makes it considerably easier to meet optical requirements, along with environmental requirements to avoid abrasion and chemical corrosion. Moreover, as guiding layer cross-section decreases, the percentage of the total power contained within the evanescent wave increases, thus increasing sensitivity per unit length. Because of this increased sensitivity per unit length, low-absorbance measurements can be made with a sensing element of reasonable length (a few centimeters). Thus, while the present invention is not limited to use of thin-films for the guiding layer, it has particular utility for use with thin-films. As an example of a thin-film suitable for use with the present invention, diamond and diamond-like carbon (DLC) are both available in film-form at reasonable cost.

Generally, suitable materials for the guiding layer or the buffer layer, if one is used, include metal oxides, nitrides, glass and polymers. Since most spectroscopy is done in the infra-red, infra-red transmitting materials are desirable.

Potential infrared transmitting materials used for both the buffer layer and the guiding layer include, but are not limited to, the following: aluminum nitride (AlN), alumina ($Al_2O_3$), aluminum oxy-nitride (AlON), barium fluoride ($BaF_2$), calcium fluoride ($CaF_2$), cadmium sulfide (CdS), lithium fluoride (LiF), magnesium fluoride ($MgF_2$), magnesium oxide (MgO), quartz, sapphire, silicon (Si), silicon nitride ($Si_3N_4$), silicon carbide (SIC), silicon monoxide (SiO), silicon dioxide ($SiO_2$), silicon oxynitride (SiON), tantalum pentoxide ($Ta_2O_5$), titanium-20 glass (Ti-20 glass), titanium carbide (TIC), titanium nitride (TIN), titanium dioxide ($TiO_2$), vanadium pentoxide ($Va_2O_5$), yttrium oxide ($Y_2O_3$), zinc oxide (ZnO), zinc sulfide (ZnS), zinc selenide (ZnSe), zirconia ($ZrO_2$), infra-red transmitting glass, such as AMTIR®, commercially available from Amorphous Materials of Garland, Tex., cubic boron nitride, diamond and thorium fluoride.

Reflection of the incident beam of radiation can be accomplished by the present invention in one of two ways: the angle of the end face can be chosen such that the incident beam of radiation is internally reflected, or the beveled end face can be coated with a reflective coating. Therefore, the waveguide of the present invention may further include a reflective coating deposited on the at least one beveled end face. Such a reflective coating is shown at 34 in FIG. 1. This latter approach of using a reflective coating is most helpful when the refractive index of the surrounding medium is close to the refractive index of the guiding layer. Suitable reflective coatings include materials such as dielectric materials, or certain metals, such as gold. In addition, a protective coating, not shown, may also be deposited on the at least one beveled end face on top of reflective coating 34 for protection against abrasion, etc. Such protective coating may also comprise a dielectric material, such as diamond.

It is noted that first surface 22a of guiding layer 22 is in contact with the medium which is being analyzed. As noted above, the waveguide sensing element of the present invention should be designed such that the surrounding medium, and the materials of all the components adjacent the guiding layer, have a lower refractive index than that of the guiding layer. It is also possible to have an additional outer layer of a protective coating on first surface 22a, as well as on beveled end faces 22c and 22d as noted above, to provide abrasion resistance or other forms of protection to the guiding layer. This protective layer should be no thicker than a few tenths of a wavelength so that the evanescent wave can extend into the sample medium.

In accordance with the present invention, an anti-reflective coating may be used to reduce reflection at the interface of the guiding layer and the buffer layer at the point of beam entry and exit. An anti-reflective coating is deposited on the surface of the substrate between the substrate and the guiding layer, or when a buffer layer is used, in the surface of the buffer layer, or both. An anti-reflective coating 36 is shown at both locations in FIG. 1. The anti-reflective coating is used between the substrate and the guiding layer, or between the buffer layer and the guiding layer, in order to reduce reflection at the interface of the substrate and the guiding layer, or between the buffer layer and the guiding layer, respectively. Anti-reflective coating can prevent unwanted signal loss due to reflection from the surface interfaces. Although not shown, optical fibers 18, 20 also may also be coated with an anti-reflective coating on the fiber ends that are adjacent to the guiding layer in order to reduce reflection and prevent unwanted signal loss at the interface of the fiber ends and the guiding layer.

The sensing element of the present invention can also act as a non-spectroscopic sensor for detecting the presence of a particular analyte in a sample medium such as a process fluid. This can be accomplished by the use of a coating on the guiding layer surface, which undergoes a physical or chemical change upon contact with the particular analyte. This change results in a measurable change in the transmission of the sensing element. Thus, a responsive coating 38 as shown in FIG. 1 may deposited on the first surface of the guiding layer. This coating may be a dielectric material, e.g., a polymer, or other material that undergoes a physical change upon contact with a particular analyte to be detected. It should be noted that if reflective coating 34 is also provided on first surface 22a, then coating 38 placed on the outer surface of coating 38 so that it is in contact with the analyte of the process fluid.

Figure 9:
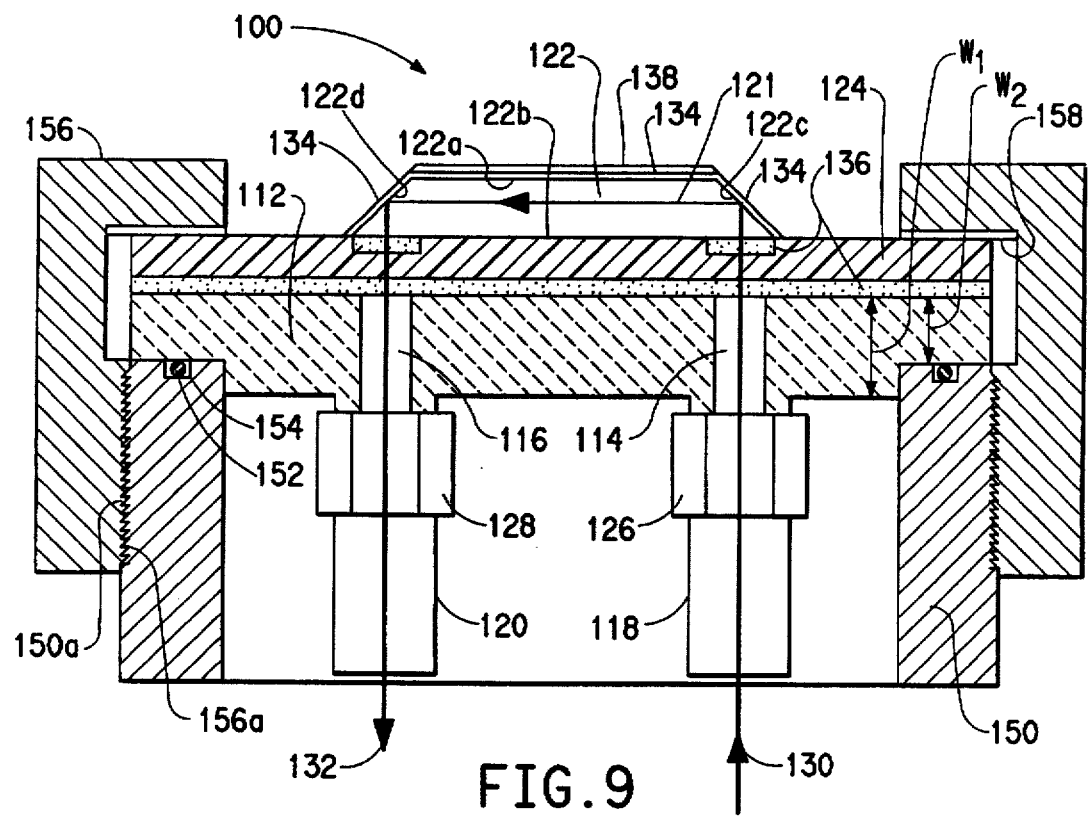
FIG. 9 is a partial, cross-sectional view of a waveguide sensing element according to a second embodiment of the present invention supported on a flange and enclosed in a protective housing which protects optical fibers from a sample medium.
Figure 10:
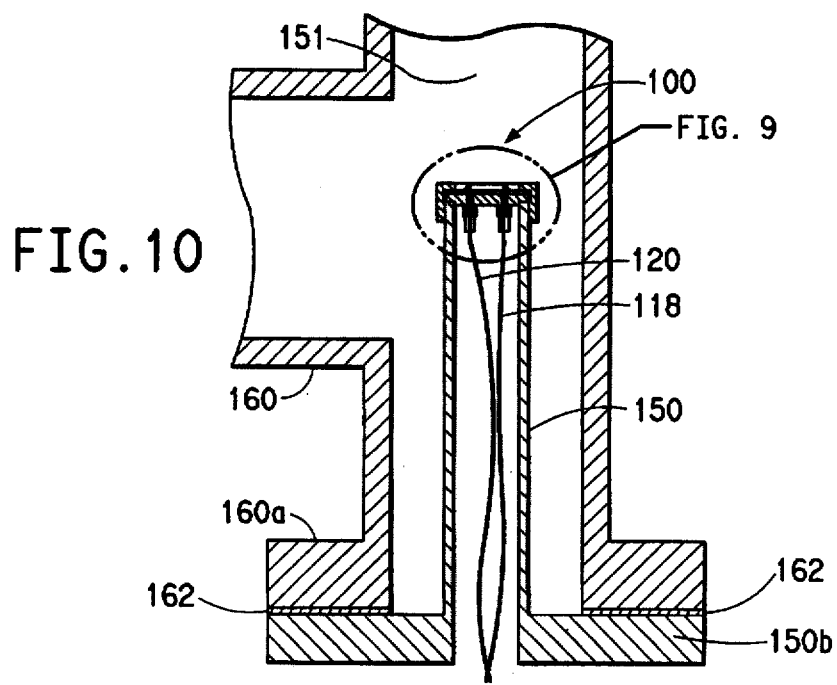
FIG. 10 is a cross-sectional view of the waveguide sensing element of FIG. 9, flange and protective housing which are positioned in a sample medium.

In accordance with a second embodiment of the present invention, there is provided a waveguide sensing element for detecting a component in a sample medium. A waveguide sensing element in accordance with the second embodiment is shown generally at 100 in FIGS. 9 and 10. The enlarged view of waveguide sensing element 100 of FIG. 10 is shown in FIG. 9. The waveguide sensing element will be described with reference numerals only respect to FIG. 9, it being understood that like elements are also shown in FIG. 10, although not numbered. This waveguide sensing element of the second embodiment is especially adapted for detecting an analyte in a corrosive process fluid in which the chemicals in the process fluid would destroy the components of the optical fibers and the sensing element. Moreover, the waveguide sensing element of the second embodiment includes a support for the sensing element, or protective housing as described more fully below, which allows for easy removal of the sensing element from the process fluid. This simplifies cleaning the waveguide sensing element when fouling occurs, or replacing the entire sensing element, if necessary.

In the second embodiment, the waveguide sensing element includes a substrate 112. As shown in FIG. 9 in particular, substrate 112 has a first portion 112a having a first width $w_1$, and a second, stepped portion 112b having a second width $w_2$ smaller than the first width. As shown in FIG. 9, substrate 112 has an input opening 114 and an output opening 116. Input opening 114 is adapted to house an input optical fiber 118, and output opening 116 is adapted to house an output optical fiber 120. The fibers are connected to the substrate by an input fiber connector 128 and an output fiber connector 126 in the same manner as described above with respect to the first embodiment, and transmit and emit electromagnetic radiation, respectively, as described above with respect to the first embodiment.

The waveguide sensing element of the second embodiment further comprises a guiding layer disposed adjacent to the substrate. As shown in FIG. 9, a guiding layer 122 is disposed adjacent to substrate 112. The waveguide sensing element of the second embodiment optionally may include a buffer layer 124 disposed between guiding layer 122 and substrate 112. The buffer layer is used if the substrate is made of a material which is not transmissive or does not have an index of refraction which is less than that of the guiding layer, as noted above for the first embodiment. Incident and exiting beams of radiation are shown at 130 and 132 in FIG. 9.

As shown in FIG. 9, the guiding layer of the second embodiment comprises a longitudinal axis 121, a first surface 122a and a second surface 122b spaced from first surface 122a. Guiding layer 122 also comprises a beveled end face extending between the first and second surfaces for directing electromagnetic radiation along the axis of the guiding layer. A plurality of beveled end faces are shown at 122c and 122d in FIG. 9. As in the first embodiment, the angle of the beveled end face may be chosen so that only modes within a given range—i.e., high order modes, are selected. Thus, the waveguide sensing element of the second embodiment is a multi-mode device that works according to the principles described above with respect to the first embodiment, and includes all the modifications thereto as discussed above. For instance, the waveguide sensing element of the second embodiment includes a reflective coating 134, identical to reflective coating 34 as described above for the first embodiment, an anti-reflective coating 136, identical to coating 36 as described above with respect to the first embodiment, and a responsive coating 138, identical to responsive coating 38 of the first embodiment. In addition, the waveguide sensing element of the second embodiment may include protective coatings on first surface 122a, as well as on beveled end faces 122c and 122d in order to provide abrasion resistance to the guiding layer.

The waveguide sensing element of the second embodiment further comprises a protective housing disposed in sealing contact with the substrate. A protective housing 150 is shown in both FIGS. 9 and 10, and in particular in FIG. 9 disposed in sealing contact with substrate 112. Fibers 118 and 120 pass through protective housing 150, as shown in particular in FIG. 10. The protective housing encases the fibers and protects the fibers from the process fluid, which is shown at 151 in FIG. 10. By sealing contact is meant contact sufficient to prevent leakage of the process fluid into the inner cavity of the protective housing. An O-ring 152 can also be used in a groove 154 adjacent to stepped portion 112b of the substrate, where protective housing 150 and substrate 112 come into sealing contact, to further ensure a tight seal between the housing and the substrate. The protective housing may have an outer threaded outer surface 150a as can be seen in particular in FIG. 9. In addition, the waveguide sensing element of the second embodiment comprises a cap 156 surrounding at least a portion of the protective housing and the substrate. Cap 156 positions the protective housing and the substrate in sealing contact with each other. The cap has an inner threaded surface 156a which mates with outer threaded surface 150a of the protective housing. A washer 158 as shown in FIG. 9 may be provided between cap 156 and substrate 112 to protect the substrate when the cap is put on the housing.

The key benefits of the arrangement of the second embodiment are that the fiber connections are located away from the process fluid and are thus protected from it. Also, a substrate, typically made of a ceramic, provides the necessary mechanical strength and chemical resistance to provide a robust seal and good thermal match for the guiding layer. The waveguide sensing element of the second embodiment can be designed to use standard pipe sizes, which provides a simple means for mounting to process piping. Such process piping is shown at 160 in FIG. 10. In this case, the protective housing may also have a flanged portion 150b as shown in FIG. 10. Process piping has a flanged portion as shown at 160a, and easily mounts to flanged portion 150b of protective housing 150. A flanged gasket 162 as shown in FIG. 10 may be disposed between protective housing flanged portion 150b and process piping flanged portion 160a to protect between these two flanged portions.

As noted above, the type of support of the waveguide sensing element of the second embodiment allows for easy removal of the sensing element from the process fluid, which simplifies cleaning the waveguide sensing element when fouling occurs, or replacing the guiding layer. It is contemplated that the sensing element of the present invention could be mass-produced cheaply enough to be essentially disposable. Sensing elements could then be disposed of when fouled and simply replaced, which is easily accomplished by the configuration of the second embodiment as shown in FIGS. 9 and 10.

It will be apparent to those skilled in the art that various modifications and variations can be made in the construction of the waveguide sensing element system of the present invention without departing from the scope or spirit of the invention. As an example, the configuration of the waveguide sensing element described above with respect to the first and second embodiments could be used as a reference sensing element, as well as a sample sensing element, where the reference and the sample sensing elements are disposed side-by-side on the same substrate in a system. By using a reference sensing element, more accurate measurements are obtained than using just one sensing element, since the reference sensing element cancels out any changes in the system common to both sensing elements. In addition, the reference and sample sensing elements could foreseeably be located on different substrates.

Further in accordance with the present invention, there is provided a method of rear-firing electromagnetic radiation. The method comprises the steps of rear-firing into a waveguide sensing element and sending the radiation into a guiding layer. The guiding layer has a longitudinal axis, a first surface, a second surface spaced from the first surface and a beveled end face extending between the first surface and the second surface, as described above with respect to FIGS. 1–10. The angle of the bevel of the beveled end face is chosen so that only modes within a given range, i.e., high order modes, are selected. As described above with respect to the first and second embodiments, such a highly sensitive waveguide sensing element is useful as an internal reflection spectroscopic sensing element. This waveguide sensing element is particularly useful in a process environment, where the corrosive effects of chemicals make on-line spectral absorption measurements difficult. Thus, with the method the present invention, the waveguide sensing element may be rear-fired, which results in the beveled end face directing rear-fired electromagnetic radiation along the longitudinal axis of the guiding layer.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A waveguide sensing element for detecting a component in a sample medium, comprising:

(a) a substrate having an input opening adapted to accept an input optical fiber and an output opening adapted to accept an output optical fiber, wherein the input optical fiber transmits rear-fired electromagnetic radiation and the output optical fiber emits the rear-fired electromagnetic radiation; and (b) a guiding layer disposed adjacent to the substrate, the guiding layer having a longitudinal axis, a first surface, a second surface spaced from the first surface and bevel means extending between the first and the second surface for directing the rear-fired electromagnetic radiation along, the longitudinal axis of the guiding layer, wherein the guiding layer has a thickness of less than 0.635 cm.

2. The sensing element of claim 1, wherein the bevel means comprises a beveled end face, wherein the beveled end face forms an angle with the second surface and the angle is chosen so that the guiding layer selects only modes within a given range.

3. The sensing element of claim 2, further including a reflective coating deposited on the beveled end face.

4. The sensing element of claim 2, further including a responsive coating deposited on the first surface of the guiding layer, wherein the responsive coating undergoes a change upon contact with a given analyte.

5. The sensing element of claim 1, further comprising a buffer layer disposed between the guiding layer and the substrate.

6. The sensing element of claim 5, wherein the guiding layer comprises zinc sulfide, the buffer layer comprises yttria and the substrate comprises alumina.

7. The sensing element of claim 5, further including an anti-reflective coating deposited on at least one of the second surface of the guiding layer and the surface of the buffer layer adjacent the substrate.

8. The sensing element of claim 1, further including a protective housing disposed in sealing contact with the substrate, wherein the housing encases the fibers and protects the fibers from the sample medium.

9. The sensing element of claim 8, further including a groove formed in the housing on a surface of the housing adjacent the substrate for receiving a seal, wherein the seal provides additional sealing contact between the housing and the substrate.

10. The sensing element of claim 8, wherein the housing has an outer threaded surface.

11. The sensing element of claim 8, further including a cap for positioning the protective housing and the substrate into sealing contact with each other, the cap surrounding at least a portion of the protective housing and the substrate.

12. The sensing element of claim 11, wherein the cap comprises a plurality of threads formed on the inner surface thereof, the cap having an inner threaded surface, wherein the inner threaded surface of the cap mates with the outer surface of the protective housing.

13. A waveguide sensing element for detecting an analyte in a process fluid, comprising:
(a) a substrate having an input opening adapted to house an input optical fiber and an output opening adapted to house an output optical fiber, wherein the input optical fiber transmits electromagnetic radiation and the output optical fiber emits the electromagnetic radiation, the substrate having a first portion with a first width and a second, stepped portion having a second width smaller than the first width;
(b) a guiding layer disposed adjacent the substrate, the guiding layer having a longitudinal axis, a first surface, a second surface spaced from the first surface and a beveled end face extending between the first surface and the second surface for directing the electromagnetic radiation along the longitudinal axis of the guiding layer;
(c) a protective housing disposed in sealing contact with the substrate and having an outer threaded surface, wherein the housing encases the fibers and protects the fibers from the process fluid; and
(d) a cap surrounding at least a portion of the protective housing for providing sealing contact between the substrate and the housing, wherein the cap has an inner threaded surface, and the inner threaded surface of the cap mates with the outer threaded surface of the protective housing.

14. The sensing element of claim 13, further including a reflective coating deposited on the beveled end face.

15. The sensing element of claim 13, further including a responsive coating deposited on the first surface of the guiding layer, wherein the responsive coating undergoes a change upon contact with a given analyte.

16. The sensing element of claim 13, further comprising a buffer layer disposed between the guiding layer and the substrate.

17. The sensing element of claim 16, wherein the guiding layer comprises zinc sulfide, the buffer layer comprises yttria and the substrate comprises alumina.

18. The sensing element of claim 16, further including an anti-reflective coating deposited on at least one of the second surface of the guiding layer and the surface of the buffer layer adjacent the substrate.

19. The sensing element of claim 13, wherein the protective housing has a flanged end, and the flanged end is adapted to be mounted to process piping.

20. A method of rear firing electromagnetic radiation, comprising the steps of:
(a) rear-firing electrogmagnetic radiation into a waveguide sensing element;
(b) sending the rear-fired radiation into a guiding layer, the guiding layer having a diameter of less than 0.635 cm and a length of less than 10 cm a longitudinal axis, a first surface, a second surface spaced from the first surface and a beveled end face extending between the first surface and the second surface;
(c) reflecting the rear-fired electromagnetic radiation off the beveled end face;
(d) directing the rear-fired electromagnetic radiation along the longitudinal axis of the guiding layer; and
(e) sending the rear-fired electromagnetic radiation out of the guiding layer.

21. A waveguide sensing element for detecting a component in a sample medium, comprising:
(a) a substrate having an input opening adapted to accept an input optical fiber and an output opening adapted to accept an output optical fiber, wherein the input optical fiber transmits rear-fired electromagnetic radiation and the output optical fiber emits the rear-fired electromagnetic radiation;
(b) a guiding layer disposed adjacent to the substrate, the guiding layer having a longitudinal axis, a first surface, a second surface spaced from the first surface and bevel means extending between the first and the second surface for directing the rear-fired electromagnetic radiation along the longitudinal axis of the guiding layer; and
(c) a buffer layer disposed between the guiding layer and the substrate, wherein the guiding layer comprises zinc sulfide, the buffer layer comprises yttria and the substrate comprises alumina.

22. A waveguide sensing element for detecting a component in a sample medium, comprising:
(a) a substrate having an input opening adapted to accept an input optical fiber and an output opening adapted to accept an output optical fiber, wherein the input optical fiber transmits rear-fired electromagnetic radiation and the output optical fiber emits the rear-fired electromagnetic radiation;
(b) a guiding layer disposed adjacent to the substrate, the guiding layer having a longitudinal axis, a first surface, a second surface spaced from the first surface and bevel means extending between the first and the second surface for directing the rear-fired electromagnetic radiation along the longitudinal axis of the guiding layer; and (c) a buffer layer disposed between the guiding layer and the substrate, wherein an anti-reflective coating is deposited on at least one of the second surface of the guiding layer and the surface of the buffer layer adjacent the substrate.

23. A waveguide sensing element for detecting a component in a sample medium, comprising:

(a) a substrate having an input opening adapted to accept an input optical fiber and an output opening adapted to accept an output optical fiber, wherein the input optical fiber transmits rear-fired electromagnetic radiation and the output optical fiber emits the rear-fired electromagnetic radiation; and (b) a guiding layer disposed adjacent to the substrate, the guiding layer having a longitudinal axis, a first surface, a second surface spaced from the first surface and bevel means extending between the first and the second surface for directing the rear-fired electromagnetic radiation along the longitudinal axis of the guiding layer;

(c) a protective housing disposed in sealing contact with the substrate, wherein the housing encases the fibers and protects the fibers from the sample medium; and (d) a cap for positioning the protective housing and the substrate into sealing contact with each other, the cap surrounding at least a portion of the protective housing and the substrate.

24. The sensing element of claim 23, wherein the cap comprises a plurality of threads formed on the inner surface thereof and the cap has an inner threaded surface, and further wherein the inner threaded surface of the cap mates with the outer surface of the protective housing.

25. A method of making a waveguide sensing element for detecting a component in a sample medium, comprising the steps of:

(a) forming an input opening adapted to accept an optical fiber and output opening adapted to accept an output optical fiber, wherein the input optical fiber transmits rear-fired electromagnetic radiation and the output optical fiber emits the rear-fired electromagnetic radiation;

(b) providing a guiding layer adjacent to the substrate, wherein the guiding layer has a longitudinal axis, a first surface and a second surface spaced from the first surface;

(c) providing a beveled end face which forms an angle with the second surface face and which extend between the first and the second surface, wherein the beveled end face directs the rear-fired electromagnetic radiation along the longitudinal axis of the guiding layer; and (d) choosing the angle formed between the beveled end face and the second surface so that the guiding layer selects only modes with a given range.

26. A method of making a waveguide sensing element for detecting a component in a sample medium, comprising the steps of:

(a) forming an input opening adapted to accept an optical fiber and output opening adapted to accept an output optical fiber, wherein the input optical fiber transmits rear-fired electromagnetic radiation and the output optical fiber emits the rear-fired electromagnetic radiation;

(b) providing a guiding layer adjacent to the substrate, wherein the guiding layer has a longitudinal axis, a first surface and a second surface spaced from the first surface;

(c) providing a lensed end face on the guiding layer which extends between the first and the second surface, wherein the lensed end face has a radius of curvature and directs the rear-fired electromagnetic radiation along the longitudinal axis of the guiding layer; and (d) choosing the radius of curvature formed between the lensed end face and the second surface so that the guiding layer selects only modes with a given range.

27. The waveguide sensing element of claim 1, wherein the guiding layer has a length of less than 10 cm.

* * * * *